United States Patent [19]

Olivieri et al.

[11] 4,389,485

[45] Jun. 21, 1983

[54] URICASE PRODUCTION METHOD

[75] Inventors: Roberto Olivieri, Mentana; Eugenio Fascetti; Pierluigi Ciuffolotti, both of Rome; Ludwig Degen, Rome, all of Italy

[73] Assignee: E.N.I. Ente Nazionale Idrocarburi, Rome, Italy

[21] Appl. No.: 294,510

[22] Filed: Aug. 20, 1981

[30] Foreign Application Priority Data

Sep. 19, 1980 [IT] Italy .............................. 24757 A/80

[51] Int. Cl.³ .......................... C12N 9/06; C12Q 1/62; C12R 1/265
[52] U.S. Cl. ..................................... 435/191; 435/10; 435/859
[58] Field of Search .......................... 435/191, 10, 859

[56] References Cited

U.S. PATENT DOCUMENTS 3,810,820  5/1974  Laboureur et al. ................. 435/191
4,062,731  12/1977  Snoke et al. ......................... 435/191
4,317,878  3/1982  Nakanishi et al. .................... 435/10

*Primary Examiner*—Lionel M. Shapiro
*Attorney, Agent, or Firm*—Hedman, Casella, Gibson, Costigan & Hoare

[57] ABSTRACT

It has been found that highly active uricase can be produced by fermentation from the microorganism *Micrococcus roseus* NRRL B 12196. The optimum activity of this microorganism is close to the pH values of the physiological liquors. The uricase so produced can be exploited in the clinical diagnostics for determining uric acid.

5 Claims, No Drawings

URICASE PRODUCTION METHOD

This invention relates to a process for the production of the uricase enzyme (EC 1.7.3.3.) with a high activity which can be exploited in the clinical diagnostics for determining uric acid in the blood serum or the urine.

Uricase is an enzyme which catalyzes the oxidation of uric acid to allantoin and is not present in the tissues of the higher mammals such as man: it is present, conversely, in the tissues, and especially in the innermost organs, of lower mammals and, in a greater of smaller amount in a few microorganisms. It has now been found, and this is the first object of the present invention, that uricase can be produced by *Micrococcus roseus*, a microorganism which was not known heretofore as producer of said enzyme and which, moreover, possesses, as compared with the other microorganisms of known type, the advantage of producing high amounts of uricase in culturing media which contain low concentrations of uric acid. It has been quite surprisingly found, furthermore, that the optimum of activity of the uricase as produced by the Micrococcus roseus NRRL B 12196 is, differently from the uricase as produced by other bacteria, close to the pH values of the physiological liquors and this is an advantage inasmuch as it is not necessary to modify the pH of the biological sample in which uric acid should be determined, so that possible hazards of chemical modifications of the sample being tested are offset. This microorganism has been isolated from a tillable land in the Monterotondo (Rome) area and possesses the following morphological and biological properties.

Microscopical Morphology

Spheres having a diameter of from 1 to 2.5 microns, immovable and Gram-positive form, by splitting on more than one plane, cubic packs or irregular groupings and sometimes they appear paired or isolated.

Macroscopical Morphology

Colonies on nutrient Agar: lifted, uninterrupted margin, rosy colour, smooth surface, 1-2 mm diameter. Slant of Agar nutrient: patina of a pale rosy hue, smooth and glossy.

Biochemical Properties

Growth in glucose broth: slight turbidity with mucoidal deposit, lightly rosy, pH =6.5.

It grows at 10° C. rather than at 45° C. optimum between 25° C. and 35° C.

It grows with glucose broth containing NaCl, at 5% and 10%, not at 15%.

Does not grow on Simmons citrate Agar.

Aerobial production of acidity from sugars in Purple Broth base (DIFCO): xylose, glycerol, mannitol, lactose, maltose, sorbose, ribose, arabinose, raffinose, cellobiose, negative; glucose, sucrose, fructose slight delayed acidification (7-10 days).

| Arginine hydrolysis: | negative |
| --- | --- |
| Starch hydrolysis: | positive |
| Gelatin hydrolysis: | negative |
| Urease: | positive |
| H$_2$S: | negative |
| Catalase: | positive |
| Nitratase: | positive |
| Indole: | negative |
| Acetoin: | negative |
| Methyl Red: | negative |
| Lecithinase: | negative |
| Lipase (butter and olive oil): | negative. |

On comparing these data with the descriptions contained in the Bergey's Manual of Determinative Bacteriology, VIII Edn. the microorganism according to the present invention belongs to the Micrococcaceae family, Micrococcus genus, sp. roseus. It has been deposited at the Northern Regional Research Center of Peoria, Ill., U.S.A., wherein it has been allotted the symbol NRRL B-12196.

The culturing of the *Micrococcus roseus* NRRL B-12196 can be carried out aerobically with any conventional method, such as in surface cultures or, better, in submerged cultures using stirred fermentors. The culturing medium, which can either be solid or liquid, contains a source of assimilable carbon, a nitrogen source, a phosphorus source as well as mineral salts and vitamins.

The cultures can be obtained at temperatures comprised between 10° C. and 40° C., the preferred range begin 25° C.-35° C., in a time of from 10 to 48 hours, preferably from 20 to 30 hours at a pH in the range 6-9, and preferably from 7 to 8.

As carbon sources there can be used, for example, glucose, lactate, acetate, sucrose, fumarate, uric acid, corn steep liquor, glycerol.

As nitrogen sources there can be used, for example: meat hydrolysates, casein or soybean hydrolysates, ammoniacal salts, urea, nitrates, uric acid.

The extraction and possible purification of uricase from the bacterial paste is made with the methods which are conventional in enzymology. The uricase extracted from *Micrococcus roseus* NRRL B-12196 can be immobilized with advantage in polymeric matrices by formation of chemical bonds with the matrix concerned, or ionic type bonds or by a mere physical immobilization. The following examples show other working modes of the present invention but are no limitations thereto.

EXAMPLE 1

A culturing broth is prepared, which has the following composition:

| Yeast extract | 15 g/l (grams per liter) |
| --- | --- |
| Uric acid | 2 g/l |

The pH was adjusted to 7.2 with NaOH and the medium was distributed in portions of 200 mls each in 500-ml flasks. After sterilization at 116° C. during 30 minutes, the flasks were inoculated with a culture of the strain NRRL B-12196 from slant containing the same medium with 2% of Agar and incubated during 24 hours at 30° C. with orbital stirring at 200 RPM. The cells were then collected by centrifuging and from 200 mls of broth there were obtained 3 g of paste (moist weight). The cellular paste thus obtained was slurried into 60 mls of phosphate buffer (0.1 M; pH=8.5) and passed through the French Pressure Cell Press until a complete cell breakdown was obtained. The enzymic activity was determined in the extract thus obtained: 1 g of moist cells contained 100 uricase units.

Dosage of uricase.

The uricase activity was determined spectrophotometrically by following the discharge of uric acid at 283 nm (nanometer) according to the method disclosed by Mahler et al, J. Biol. Chem., (1955), 216, 625, modified as reported hereinafter. 7 mls of a solution containing 20 mg of uric acid in 100 mls of phosphate buffer (0.1 M, pH=8.5) were placed in a small flask of the capacity of 50 mls and placed to incubate at 30° C. on a stirred water bath. The reaction started with the addition of a small amount of enzymic extract. Immediately after the addition of the extract and also after 10 minutes of reaction, 0.5-ml samples of the reaction mixture were drawn and added to 4 mls of 0.1 M HCl.

The absorbance of the solutions thus obtained was read out at 283 nm.

A uricase unit is defined as being the amount of enzyme which is capable of degrading 1 micromol of uric acid per minute under the test conditions specified just now.

EXAMPLE 2

An extract of Micrococcus roseus NRRL B-12196 cells has been prepared as specified in Example 1.

The raw extract was centrifuged and, on the supernatant, the activity of uricase was determined as described hereinbefore, utilizing uric acid dissolved in solutions of phosphates at 0.1 M and different pH values as the reaction mixture. There were simultaneously determined the activity of enzymic extract as obtained from cultures of Bacillus fastidiosus under the same culturing conditions as for Micrococcus roseus in question. The results which have been obtained are tabulated in Table 1 wherein the activities of the extracts of the two microorganisms at a pH of 9 have been assumed to be 100.

TABLE 1

| Uricase activity as a function of pH in extracts of B. fastidiosus and M. roseus. | | |
|---|---|---|
| pH of the reaction mixture | Extract of | |
| | M. roseus | B. fastidiosus |
| 6.5 | 71 | 13.5 |
| 7.0 | 94 | 35 |
| 7.5 | 103 | 57 |
| 8.0 | 106 | 85 |
| 8.5 | 103 | 95 |
| 9.0 | 100 | 100 |

We claim:

1. A process for the production of uricase comprising the step of culturing the microorganism Micrococcus roseus NRRL B-12196 under aerobial conditions in the presence of a culturing medium containing a source of assimilable carbon, a nitrogen source, a phosphorus source and mineral salts.

2. Process for the production of uricase according to claim 1, characterized in that the culturing temperature is comprised between 10° C. and 40° C.

3. Process for the production of uricase according to claim 2, characterized in that the culturing temperature is preferably comprised between 25° C. and 35° C.

4. Process for the production of uricase according to claim 3 characterized in that the pH of the culturing medium is comprised between 6 and 9.

5. Process for the production of uricase according to claim 4, characterized in that the pH of the culturing medium is preferably comprised between 7 and 8.

* * * * *